(12) United States Patent
Samuelsson

(10) Patent No.: US 9,592,009 B2
(45) Date of Patent: Mar. 14, 2017

(54) INTERFACE UNIT AND A MEASUREMENT SYSTEM

(75) Inventor: Magnus Samuelsson, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 613 days.

(21) Appl. No.: 14/000,750

(22) PCT Filed: Feb. 24, 2012

(86) PCT No.: PCT/EP2012/053157
§ 371 (c)(1),
(2), (4) Date: Aug. 21, 2013

(87) PCT Pub. No.: WO2012/113904
PCT Pub. Date: Aug. 30, 2012

(65) Prior Publication Data
US 2013/0324806 A1  Dec. 5, 2013

Related U.S. Application Data

(60) Provisional application No. 61/446,568, filed on Feb. 25, 2011.

(30) Foreign Application Priority Data

Feb. 25, 2011  (SE) ...................... 1150174

(51) Int. Cl.
*A61B 5/00*  (2006.01)
*A61B 18/00*  (2006.01)
(Continued)

(52) U.S. Cl.
CPC .......... *A61B 5/6876* (2013.01); *A61B 5/0002* (2013.01); *A61B 5/0215* (2013.01);
(Continued)

(58) Field of Classification Search
CPC ............... A61B 5/6876; A61B 5/0015–5/0017
See application file for complete search history.

(56) References Cited

U.S. PATENT DOCUMENTS 4,288,854 A * 9/1981 Burroughs ............. G05D 23/24
                                                    165/253
5,117,113 A * 5/1992 Thomson ................ G01T 1/026
                                                    250/370.07
(Continued)

FOREIGN PATENT DOCUMENTS

EP   1 055 392 B1   11/2000
JP   06-186103 A    7/1994
(Continued)

OTHER PUBLICATIONS

Canadian Office Action for 2,827,570, EP2012053157, dated Mar. 17, 2015.
(Continued)

*Primary Examiner* — Gary Jackson
*Assistant Examiner* — Amanda Steinberg
(74) *Attorney, Agent, or Firm* — Foley & Lardner LLP

(57) ABSTRACT

The present invention relates to an extracorporeale interface unit (8), for an intravascular measurement system for measuring at least one physiological, or other, variable in a living body, adapted to generate a sensor signal in response of the variable. The interface unit (8) comprises a sensor interface circuitry (6) adapted to interface a sensor wire configured to be inserted into the living body and provided with one or many sensor element(s) at its distal region. The sensor interface circuitry (6) comprises a measurement unit (9) adapted to generate the measured data of the variable as a sensor signal. The interface unit (8) further comprises a control unit (1) adapted to control and supervise the different functions of the interface unit (8), wherein the different (Continued)

functions are performed by predefined tasks (T1, T2 ... TN) during consecutive control periods CP having the same time duration.

15 Claims, 5 Drawing Sheets

(51) Int. Cl.
    *A61N 1/00*     (2006.01)
    *A61B 5/0215*     (2006.01)
    *A61B 5/01*     (2006.01)
    *A61B 5/02*     (2006.01)
    *A61B 5/026*     (2006.01)

(52) U.S. Cl.
    CPC .......... *A61B 5/4836* (2013.01); *A61B 5/6851* (2013.01); *A61B 5/7203* (2013.01); *A61B 5/7225* (2013.01); *A61B 18/00* (2013.01); *A61N 1/00* (2013.01); *A61B 5/01* (2013.01); *A61B 5/02* (2013.01); *A61B 5/026* (2013.01); *A61B 5/7217* (2013.01); *A61B 2018/00708* (2013.01); *A61B 2560/0252* (2013.01); *A61B 2560/045* (2013.01); *A61B 2562/227* (2013.01)

(56) References Cited

U.S. PATENT DOCUMENTS

| | | |
|---|---|---|
| 5,357,956 A | 10/1994 | Nardella |
| 5,515,295 A * | 5/1996 | Wang .................... G01F 1/6845 702/113 |
| 5,568,815 A | 10/1996 | Raynes et al. |
| 5,668,320 A | 9/1997 | Cowan et al. |
| 6,112,598 A | 9/2000 | Tenerz et al. |
| 6,171,252 B1 | 1/2001 | Roberts |
| 6,586,943 B1 | 7/2003 | Masuda et al. |
| 7,207,227 B2 | 4/2007 | Rangsten et al. |
| 7,724,148 B2 | 5/2010 | Samuelsson et al. |
| 2002/0134163 A1* | 9/2002 | Clifford .............. G01L 19/0038 73/715 |
| 2002/0173724 A1 | 11/2002 | Dorando et al. |
| 2003/0163052 A1 | 8/2003 | Mott et al. |
| 2004/0012379 A1 | 1/2004 | Van Deursen et al. |
| 2004/0225184 A1 | 11/2004 | Shimizu et al. |
| 2006/0009817 A1 | 1/2006 | Tulkki |
| 2007/0043298 A1* | 2/2007 | Plouf .................... A61B 5/0031 600/485 |
| 2007/0255144 A1 | 11/2007 | Tulkki et al. |
| 2008/0033254 A1* | 2/2008 | Kamath ............. A61B 5/14532 600/300 |
| 2008/0200770 A1 | 8/2008 | Hubinette |
| 2009/0124880 A1 | 5/2009 | Smith |
| 2010/0268038 A1 | 10/2010 | Smith |
| 2010/0331916 A1 | 12/2010 | Parramon et al. |

FOREIGN PATENT DOCUMENTS

| | | |
|---|---|---|
| JP | 10-505269 A | 5/1998 |
| JP | 10-267779 A | 10/1998 |
| JP | 2000-504249 A | 4/2000 |
| JP | 2001-33330 A | 2/2001 |
| JP | 2007-000244 A | 1/2007 |
| JP | 2009-504357 A | 2/2009 |
| JP | 2009-136675 A | 6/2009 |
| JP | 2010-518900 A | 6/2010 |
| WO | WO 96/07351 A1 | 3/1996 |
| WO | WO 97/27802 A1 | 8/1997 |
| WO | WO 02/094339 A2 | 11/2002 |
| WO | WO 2004/096022 A1 | 11/2004 |
| WO | WO 2007/022620 A2 | 3/2007 |
| WO | WO 2008/100208 A1 | 8/2008 |
| WO | WO 2008/128350 A1 | 10/2008 |

OTHER PUBLICATIONS

Canadian Office Action for 2,816,915, EP2011069728, dated Feb. 3, 2015.
Swedish Office Action and International-Type Search Report dated Aug. 26, 2011, 9 pgs.
Japanese Office Action and English language translation dated May 13, 2014, 7 pgs.
Australian Office Action dated Jul. 2, 2014, 8 pgs.
Japanese Office Action and English language translation dated Aug. 26, 2014, 11 pgs.
U.S. Appl. No. 13/884,471, filed May 9, 2013, Samuelsson.
USPTO Office Action, U.S. Appl. No. 13/884,471, Sep. 7, 2016 (2002/0059827, 2003/0125790, 2006/0207335, 2006/0009817, 2007/0106165, 2007/0142727, 2008/0033254, 2008/0200770, 2009/0299157, 2012/0271178, 2015/0313478, U.S. Pat. No. 5,544,651, U.S. Pat. No. 5,967,986, U.S. Pat. No. 6,248,083, U.S. Pat. No. 6,409,677, U.S. Pat. No. 6,565,514, U.S. Pat. No. 6,586,943, U.S. Pat. No. 6,712,772, U.S. Pat. No. 7,413,547, U.S. Pat. No. 4,915,113, U.S. Pat. No. 4,911,167, U.S. Pat. No. 6,171,252, 2002/0173724, 2008/0033254).

\* cited by examiner

INTERFACE UNIT AND A MEASUREMENT SYSTEM

FIELD OF THE INVENTION

The present invention relates to an interface unit and a measurement system comprising said interface unit according to the preambles of the independent claims.

BACKGROUND OF THE INVENTION

In many medical procedures, various physiological conditions present within a body cavity need to be monitored. These physiological conditions are typically physical in nature such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient.

In the prior art, it is known to mount a sensor at a distal portion of a so-called sensor wire and to position the sensor by using the sensor wire in a blood vessel in a living body to detect a physical parameter, such as pressure or temperature. The sensor includes elements that are directly or indirectly sensitive to the parameter.

One known sensor wire has a typical length of 1.5-2 meter, and comprises a hollow tubing running along a major part of the wire and having an outer diameter in the range of 0.25-0.5 mm, typically approximately 0.35 mm. A core wire is arranged within the tubing and extends along the tubing and often extends out from a distal opening of the tubing. The sensor or sensors is/are preferably arranged in connection with the distal portion of the core wire, e.g. at the distal end of the sensor wire.

The present invention is e.g. applicable in relation with a sensor wire of the type described above.

In one application the sensor wire of the type described above is used to measure pressure in blood vessels, and in particular in the coronary vessels of the heart, e.g. to identify constrictions in the coronary vessels for example by determining the so-called Fractional Flow Reserve related to the vessel. The sensor wire is typically inserted by use of an insertion catheter, which in turn is inserted via the femoral vein or the radial artery, and guided by the inserted catheter to the measurement site.

In order to power the sensor and to communicate signals representing the measured physiological variable to an external physiology monitor, one or more cables or leads, often denoted microcables, for transmitting the signals are connected to the sensor, and are routed along the sensor wire to be passed out from the vessel to the external physiology monitor, via physical cables or wirelessly.

The sensor element further comprises an electrical circuitry, which generally is connected in a Wheatstone bridge-type of arrangement to one or several piezoresistive elements provided on a membrane. As is well known in the art, a certain pressure exerted on the membrane from the surrounding medium will thereby correspond to a certain stretching or deflection of the membrane and thereby to a certain resistance of the piezoresistive elements mounted thereon and, in turn, to a certain output from the sensor element.

In U.S. 2006/0009817 A1, which is incorporated herein in its entirety, and which is assigned to the present assignee, an example of such a sensor and guide wire assembly is disclosed. The system comprises a sensor arranged to be disposed in the body, a control unit arranged to be disposed outside the body and a wired connection between the sensor and the control unit, to provide a supply voltage from the control unit to the sensor and to communicate a signal there between. The control unit further has a modulator, for modulating the received sensor signal and a communication interface for wireless communication of the modulated signal.

In U.S. Pat. No. 7,724,148 B2, which is incorporated herein in its entirety, and which also is assigned to the present assignee, another example of such pressure measurement system is disclosed. The pressure sensor wire is adapted to be connected, at its proximal end, to a transceiver unit that is adapted to wirelessly communicate via a communication signal with a communication unit arranged in connection with an external device.

In U.S. Pat. No. 6,112,598 A, which is incorporated herein in its entirety, and assigned to the present assignee, and also in U.S. Pat. No. 7,207,227 B2 further examples of such pressure sensors and guide wire assemblies are disclosed.

Thus, the interface unit, the system according to the present invention are applicable in sensor wire assemblies as disclosed in the above-referenced patents and patent application.

It is an object of the invention to provide an improved interface unit comprising a sensor interface circuit with lower noise.

A further object is to provide an improved interface unit comprising a sensor interface circuitry which provides maintained high signal output, but which reduces sensor power dissipation and lowered self-heating.

SUMMARY OF THE INVENTION

The above-mentioned objects are achieved by the present invention according to the independent claim.

Preferred embodiments are set forth in the dependent claims.

According to a first aspect, the present invention relates to an extracorporeale interface unit, for an intravascular measurement system for measuring a physiological, or other, variable in a living body, being adapted to generate a sensor signal in response of a variable. The interface unit comprises a sensor interface circuitry adapted to interface a sensor wire configured to be inserted into the living body and provided with one or many sensor element(s) at its distal region. The sensor interface circuitry comprises a measurement unit adapted to generate the measured data of the variable as a digital sensor signal. The interface unit further comprises a control unit adapted to control and supervise the different functions of the interface unit, wherein the different functions are performed by predefined tasks during consecutive control periods having the same time duration. During each task a predefined function of the interface unit is performed. Each predefined task has a designated task time period length, and only one task is adapted to be executed at the same time, and each task in a control period has a designated task time slot within said control period. The tasks within a control period are separated by a specified task separation time period.

The present invention is based on the insight that keeping timeslots for measurements separated in time from radio transmissions or other electrical activity provides lower level of disturbing noise that might compromise the measurements.

According to another aspect, the present invention is based on the insight that if the energy sources are only switched on for short durations of time when different functions are being performed and switched off otherwise, the average sensor power dissipation is reduced accordingly.

Thus, the present invention is applicable in connection with the use of switched current sources or, as an alternative, in connection with matched resistors when performing the measurements.

According to a second aspect, the present invention further relates to a measurement system comprising such an extracorporeale interface unit.

SHORT DESCRIPTION OF THE APPENDED DRAWINGS

DETAILED DESCRIPTION OF PREFERRED EMBODIMENTS OF THE INVENTION

The present invention relates to an interface unit 8 adapted to be arranged in e.g. a transceiver unit, e.g. the PressureWire™ Aeris™ (trademarks owned by the applicant) transmitter, or a connector unit adapted to be connected to the proximal end of a sensor wire provided, at its distal end, with a sensor to measure a variable in a living body. When the sensor element of the sensor is placed in fluid communication within a body cavity, a certain pressure exerted on a membrane of the sensor element from the surrounding medium will correspond to a certain stretching or deflection of the membrane and thereby to a certain resistance of the piezoresistive elements mounted thereon and, and in turn, to a certain output from the sensor element which is communicated to the interface unit.

Figure 1:
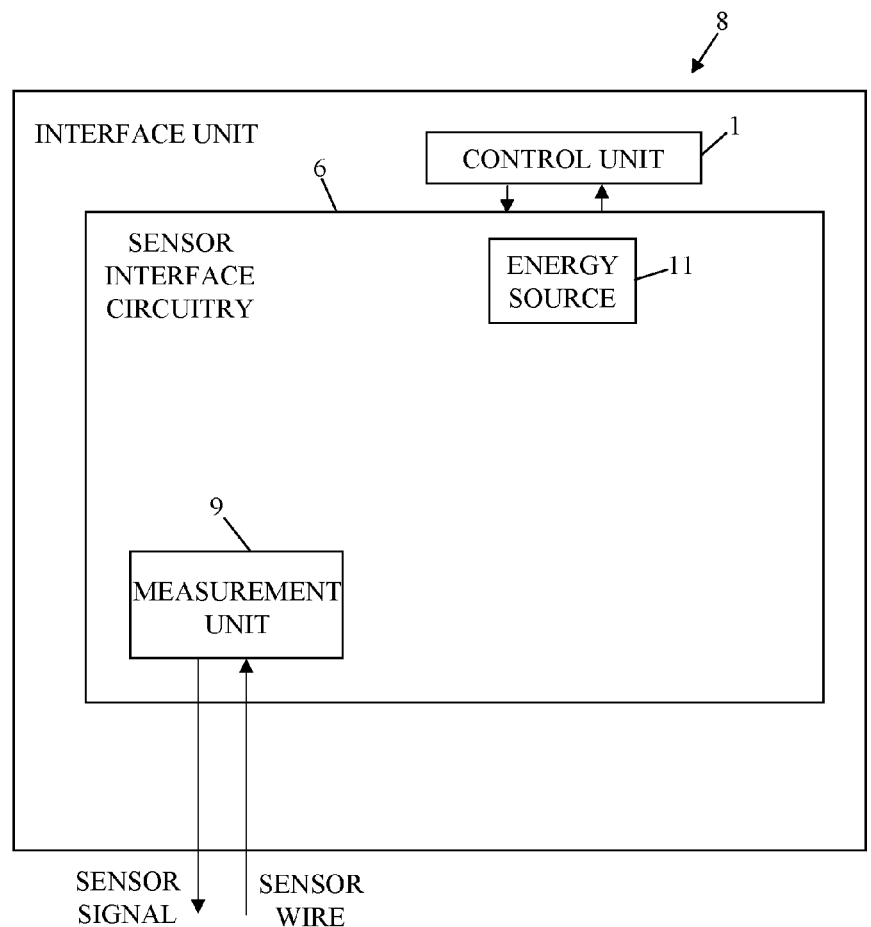
FIG. 1 shows a block diagram schematically illustrating the interface unit according to one embodiment of the present invention.

FIG. 1 shows a block diagram schematically illustrating the extracorporeale interface unit 8, for an intravascular measurement system for measuring at least one physiological, or other, variable in a living body, adapted to generate a sensor signal in response of the variable, according to one embodiment of the present invention. As illustrated in FIG. 1, the interface unit 8 comprises a sensor interface circuitry 6 adapted to interface a sensor wire (not shown) configured to be inserted into the living body and provided with one or many sensor element(s) at its distal region, the sensor interface circuitry 6 comprises a measurement unit 9 adapted to generate the measured data of the variable as a sensor signal. The interface unit 8 comprises a control unit 1 adapted to control and supervise the different functions of the interface unit 8.

Figure 2:
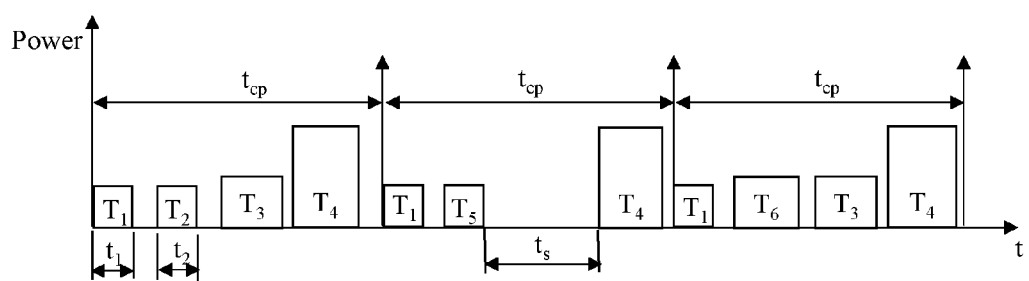
FIG. 2 shows a sampling scheme illustrating three consecutive control periods for the interface unit.

The different functions are performed by predefined tasks $T_1, T_2 \ldots T_n$ during consecutive control periods CP having the same time duration $t_{cp}$, as shown in FIG. 2. During each task $T_1, T_2 \ldots T_n$ a predefined function of the interface unit 8 is performed. Each predefined task $T_1, T_2 \ldots T_n$ has a designated task time period length $t_1, t_2, t_3, \ldots t_n$, and only one task $T_1, T_2 \ldots T_n$ is adapted to be executed at the same time, and each task $T_1, T_2 \ldots T_n$ in a control period CP has a designated task time slot within the control period CP, and the tasks $T_1, T_2 \ldots T_n$ within a control period CP are separated by a specified task separation time period $t_s$.

According to one embodiment, the different functions includes one or many of, measuring the at least one variable, processing measured data, performing radio communication with external devices, performing electrical stimulation of tissue, or performing ablation of tissue.

In FIG. 2, the first control period CP comprises four different predefined tasks $T_1, T_2, T_3, T_4$. Each predefined task $T_1, T_2, T_3, T_4$ corresponds to the execution of a function of the interface unit 8. The second control period CP comprises three different predefined tasks $T_1, T_4, T_5$, etc. Thus, the different functions do not need to be performed every control period CP. In some cases it is sufficient to perform specific tasks, e.g. a measurement or other function, every second, third or fourth control period CP, and even with longer durations between the specific task is executed. This depends naturally of the nature of the variable to be measured or which other function is to be performed. For example, if a temperature is to be measured it is often sufficient to measure the temperature at fewer instances compared to the case where pressure is to be measured because the temperature normally changes much slower than the pressure.

In one embodiment, a predefined task $T_1, T_2 \ldots T_n$ has a designated execution frequency rate of 50-500 Hz. The designated execution frequency rate states if the predefined task $T_1, T_2 \ldots T_n$ is executed every control period CP, or every second control period CP, or every third control period CP, or every fourth control period CP, etc.

In one embodiment, the function measuring of the variable is executed at approximately a 50-500 Hz rate. In one embodiment, processing measured data is executed at a 400 Hz rate. Radio communication with external devices may be performed at approximately a 400 Hz rate. Electrical stimulation of tissue may be performed approximately at a 1-200 Hz rate. Ablation of tissue may be performed at a 10-500 Hz rate.

The sensor interface circuitry 6 is adapted to be energized by at least one energy source 11. According to one embodiment the energy source 11 is switched off during the task separation time period $t_s$. If the energy source 11 is switched off during the task separation time period $t_s$ as to be on only for short durations of time when a predefined task $T_1, T_2 \ldots T_n$ of interest is performed but switched off otherwise, the average sensor power dissipation is reduced accordingly which lowers self-heating of the sensor element while still providing high signal output.

The average sensor power $P_{average}$ can thus be reduced by:

$$P_{average} = P_{sensor} \frac{t_n}{t_{cp}}$$

$$t_n \leq t_{cp}$$

$$P_{sensor} = R_{sensor} I_{source}^2$$

Where $P_{sensor}$ is the momentary power delivered to the sensor, $t_n$ is the time when the energy source is switched on and $t_{cp}$ is the duration of a control period CP. The task separation time period $t_s$ is approximately 10-1000 µs.

In one embodiment of the present invention, the sensor interface circuitry 6 uses a high-precision matched resistor pair ($R_B$, $R_B$) in a Wheatstone bridge-type circuit excited from a constant voltage source when measuring a variable. The Wheatstone bridge-type circuit comprises an active resistor $R_A$ and a passive resistor R. The Wheatstone bridge-type circuit is adapted to be connected to piezoresistive elements mounted on a membrane of the sensor element of a sensor wire.

Figure 3:
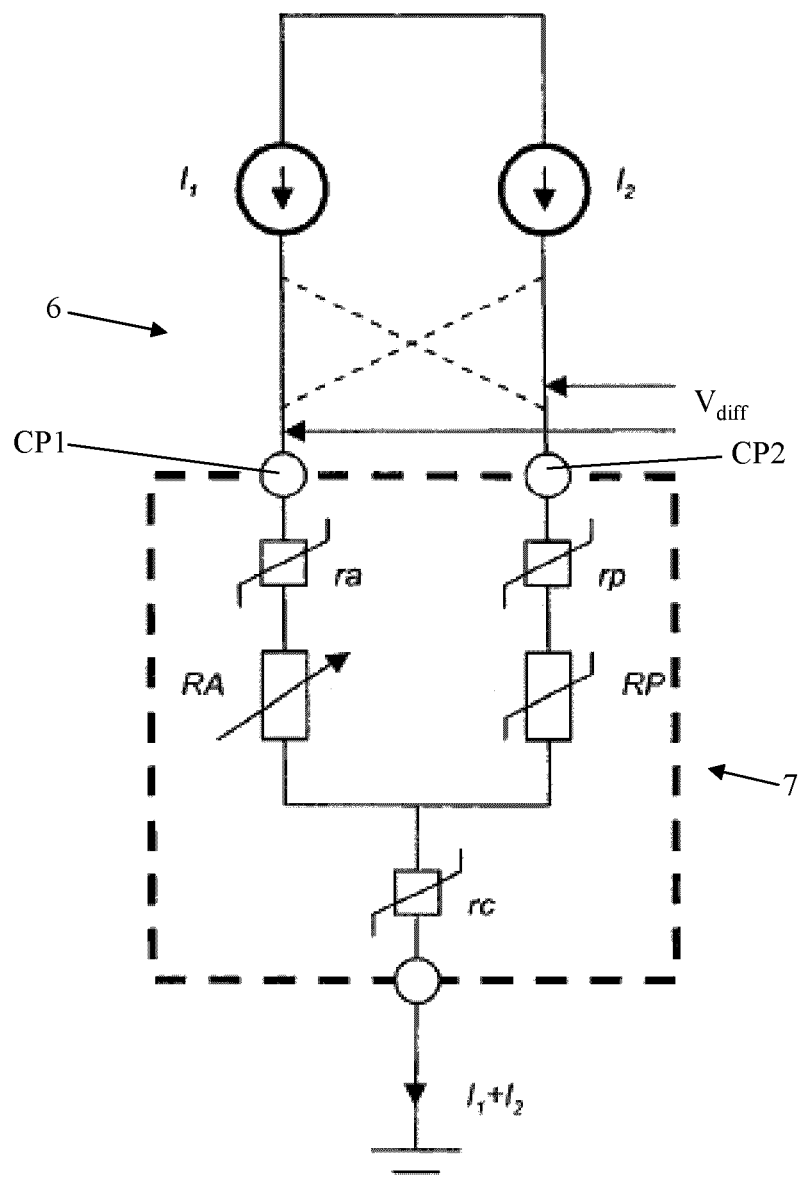
FIG. 3 shows a sensor interface circuitry comprising switched current sources adapted to be arranged in an interface unit according to one embodiment of the present invention.

According to another embodiment, as illustrated in FIG. 3, the sensor interface circuitry 6 uses two current sources, generating two currents $I_1$, $I_2$, adapted to energize a sensor element (not shown) of a sensor wire 7. Thus, the sensor interface circuitry 6 is, via at least two connection points CP1, CP2, adapted to be connected to the proximal end of a sensor wire 7 provided, at its distal end, with a sensor to measure a physiological, or other, variable in a living body. The sensor interface circuitry 6 comprises two current sources CSU1, CSU2, generating a first and a second current $I_1$, $I_2$ of which the connections are alternately switched (illustrated by dotted lines, in FIG. 3) between two of the connection points CP1, CP2. This is advantageous when measuring the at least one variable in that by taking average readings $V_{diff}$ between the consecutive switching states, the effect of offset currents due to temperature drift is cancelled.

Figure 4:
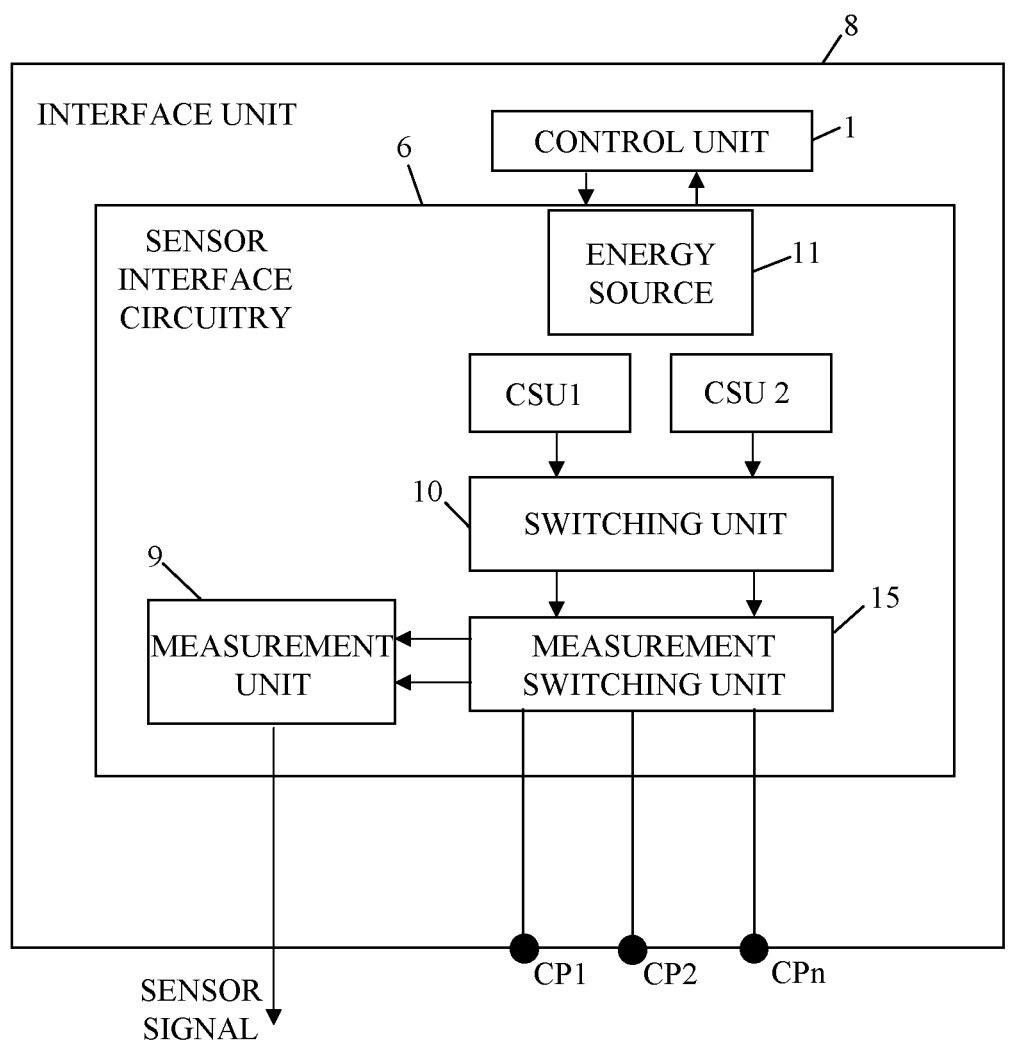
FIG. 4 shows a block diagram schematically illustrating the interface unit comprising switched current sources according to one embodiment of the present invention.

According to the embodiment shown in FIG. 4, the extracorporeale interface unit 8 with the sensor interface circuitry 6 comprising two current source units CSU1, CSU2 is schematically illustrated. The extracorporeale interface unit 8, is adapted to generate a digital sensor signal in response of a variable. The interface unit 8 comprises a sensor interface circuitry 6 adapted to interface a sensor wire (not shown) configured to be inserted into the living body and provided with one or many sensor element(s) at its distal region. The interface unit 8 comprises a control unit 1 adapted to control and supervise the different functions of the interface unit 8. The sensor interface circuitry 6 further comprises a measurement unit 9 adapted to generate the measured data of the variable as a digital sensor signal. The current source units CSU1, CSU2 are adapted to energize the sensor element(s) via at least two connection points CP1, CP2, . . . CPn. The sensor interface circuitry 6 further comprises a switching unit 10, wherein the switching unit 10 is adapted to alternately switch connection between the current source units CSU1, CSU2 and at least two of the connection points CP1, CP2, . . . CPn from one control period CP to a subsequent control period CP. Each connection is maintained during one of the predefined tasks $T_1$, $T_2$ . . . $T_n$, having a task time period length $t_1$, $t_2$ . . . , $t_n$.

Furthermore, in FIG. 4, a measurement switching unit 15 adapted to switch connection points CP1, CP2, . . . CPn depending on which variable is to be measured, is shown.

In one embodiment, the task time period length $t_1$, $t_2$ . . . , $t_n$ is essentially the same for each connection, and the measurement unit 9 is adapted to determine a sensor variable value $V_{diff}$ related to the variable at two of the connection points CP1, CP2, . . . CPn. The sensor signal is related to the average value of sensor variable values $V_{diff}$ from at least two task time period lengths $t_1$, $t_2$ . . . , $t_n$.

Thus, the switched current source units CSU1, CSU2 are preferably used in connection with measuring the at least one variable. The energy source 11 is further adapted to energize one or many of the functions including processing measured data, performing radio communication with external devices, performing electrical stimulation of tissue, or performing ablation of tissue.

According to one embodiment, in a similar way as described above, the two current source units CSU1, CSU2 are switched in time so as to be on only for short durations of time when measuring the signal of interest is performed but switched off otherwise during the task separation time period $t_s$.

The time duration of the control periods CP may be between 0.5-20 ms. In one embodiment, the time duration of the control periods CP is approximately 2.5 ms.

Figure 5:
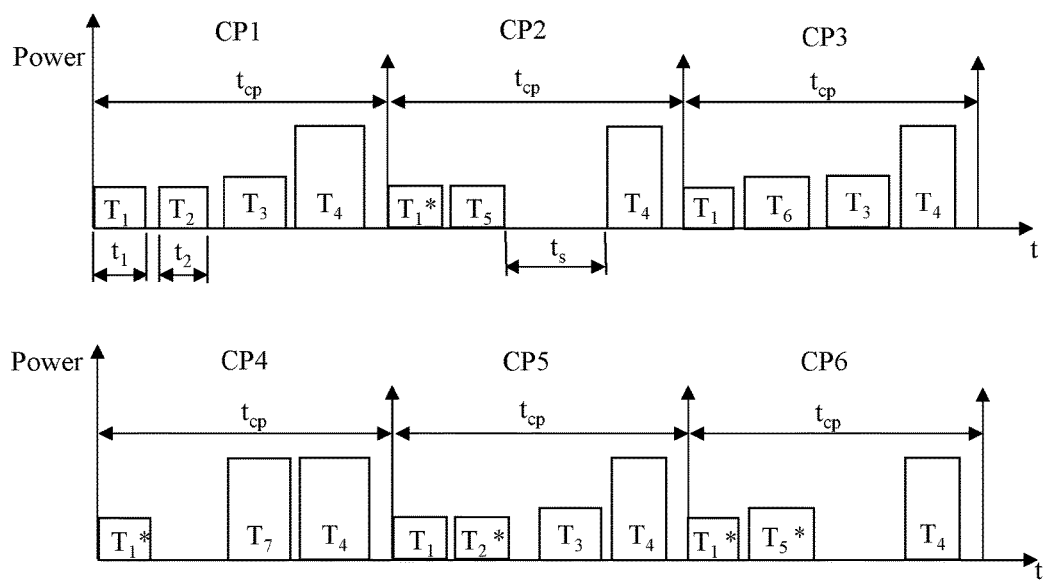
FIG. 5 shows a sampling scheme illustrating six consecutive control periods when using switched current sources for the interface unit.

In FIG. 5, a sampling scheme illustrating six consecutive control periods CP1, CP2, . . . , CP6 for the interface unit 8, is shown. The control periods CP are divided into a number of periods for performing different functions, where each period is designated a predefined tasks $T_1$, $T_2$ . . . $T_n$ having a task time period length $t_1$, $t_2$ . . . $t_n$. For example, if more than one sensor is used, each sensor may be designated a separate period. In FIG. 5, the first control period CP comprises four different predefined tasks $T_1$, $T_2$, $T_3$, $T_4$. The asterisk (*) denotes that the currents sources are switched. Thus, in the first control period CP1 during task $T_1$ measurements of a variable is performed, and in the second control period CP2 during task $T_1$* measurements of the same variable is performed again, however, switching of the current sources has been performed therebetween. FIG. 5 further illustrates that the measurements and other functions do not need to be performed every control period CP. Thus, in some cases it is sufficient to perform a measurement or other function e.g. every second, third or fourth control period CP. Consequently, if a measurement is performed every fourth control period CP, e.g. task $T_2$ in CP1 and CP5, the switching is also performed every fourth control period CP.

Figure 6:
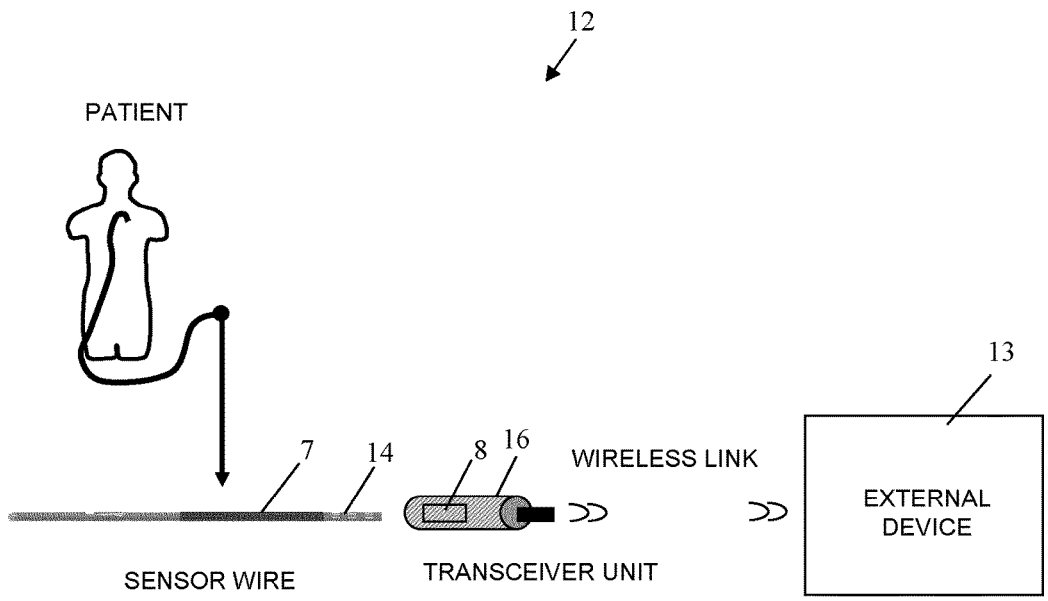
FIG. 6 shows a measurement system, comprising an interface unit arranged in a transceiver unit, according to the present invention.

In FIG. 6, a measurement system 12, for intravascular measurements of at least one physiological, or other, variable in a living body, is schematically shown. The measurement system 12 comprises a sensor wire 7, adapted to be inserted into the body, comprising a sensor element (not shown) arranged in a distal region of the sensor wire 7, an external device 13, adapted to receive measured data The measurement system 12 comprises an extracorporale interface unit 8 adapted to be connected to a proximal end 14 of the sensor wire 7. As shown in FIG. 6, the interface unit 8 is adapted to generate a sensor signal in response of a variable, which measured data is transferred to an external device 13. The interface unit 8 is arranged in a transceiver unit 16 adapted to transfer the sensor signal via a wireless connection to an external device 13.

Figure 7:
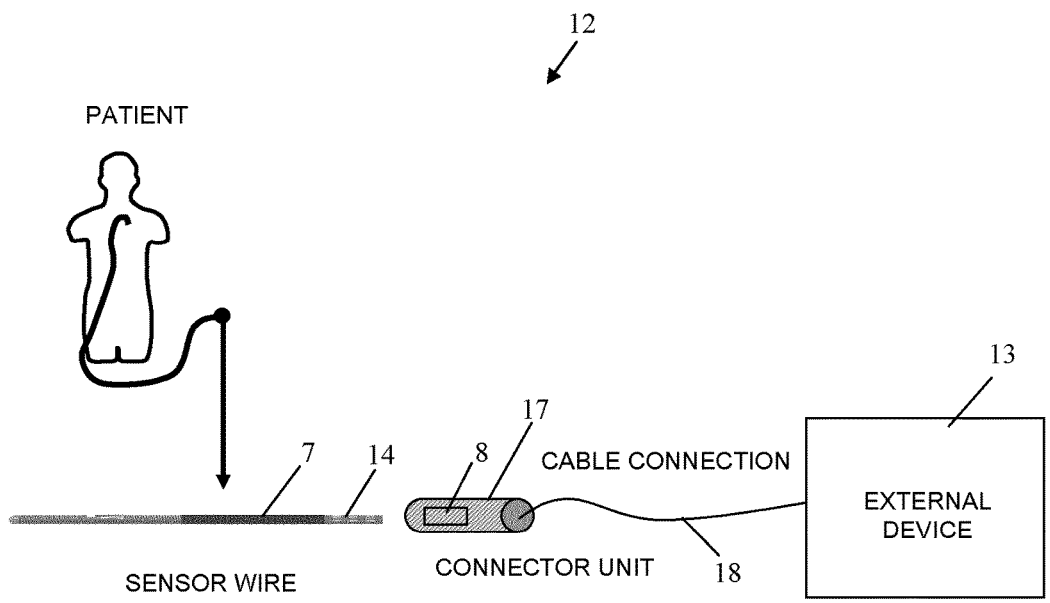
FIG. 7 shows a measurement system, comprising an interface unit arranged in a connector unit, according to the present invention.

In another embodiment, illustrated by FIG. 7, the interface unit 8 is arranged in a connector unit 17 adapted to transfer the sensor signal via a cable connection 18 to an external device 13.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. An extracorporeale interface unit, for an intravascular measurement system for measuring at least one physiological, or other, variable in a living body, adapted to generate a sensor signal in response to said variable, which interface unit comprises:
   a sensor interface circuitry adapted to interface a sensor wire configured to be inserted into the living body and provided with one or more sensor elements at its distal region, the sensor interface circuitry being configured to generate measured data of said variable as a sensor signal;
   a controller configured to control and supervise functions of the interface unit, wherein the functions are performed by predefined tasks ($T_1, T_2, \ldots, T_n$) during consecutive control periods having the same time duration $t_{cp}$, and that during each task ($T_1, T_2, \ldots, T_n$) a predefined function of the interface unit is performed, wherein each predefined task ($T_1, T_2, \ldots, T_n$) has a designated task time period length ($t_1, t_2, t_3, \ldots, t_n$), and only one task ($T_1, T_2, \ldots, T_n$) is adapted to be executed at the same time and each task ($T_1, T_2, \ldots, T_n$) in a control period has a designated task time slot within said control period, wherein the tasks ($T_1, T_2, \ldots, T_n$) within a control period are separated by a specified task separation time period $t_s$ and
   wherein said sensor interface circuitry comprises two distinct current source units (CSU1, CSU2) adapted to energize said one or more sensor elements via at least two connection points (CP1, CP2, . . . , CPn), and a switching unit, wherein said switching unit is adapted to alternately switch connection between said current source units (CSU1, CSU2) and at least two of said connection points (CP1, CP2, . . . , CPn) from one control period to a subsequent control period, and wherein each connection is maintained during one of said predefined tasks ($T_1, T_2, \ldots, T_n$), having a task time period length ($t_1, t_2, t_3, \ldots, t_n$).

2. The interface unit according to claim 1, wherein said functions include one or more of, measuring said at least one variable, processing measured data, performing radio communication with external devices, performing electrical stimulation of tissue, or performing ablation of tissue.

3. The interface unit according to claim 1, wherein a predefined task ($T_1, T_2 \ldots T_n$) has a designated execution frequency rate of 50-500 Hz.

4. The interface unit according to claim 1, wherein said designated execution frequency rate determines if the predefined task ($T_1, T_2 \ldots T_n$) is executed every control period, or every second control period, or every third control period, or every fourth control period, etc.

5. The interface unit according to claim 1, wherein said circuitry is adapted to be energized by at least one energy source.

6. The interface unit according to claim 5, wherein said energy source is switched off during said task separation time period $t_s$.

7. The interface unit according to claim 1, wherein said task separation time period $t_s$ is approximately 10-1000 µs.

8. The interface unit according to claim 1, wherein said task time period length ($t_1, t_2, t_3, \ldots, t_n$) is essentially the same for each connection, and that said sensor interface circuitry is adapted to determine a sensor variable value ($V_{diff}$) related to said variable at two of said connection points (CP1, CP2, . . . CPn).

9. The interface unit according to claim 8, wherein said sensor signal is related to average value of sensor variable values ($V_{diff}$) from at least two task time period lengths ($t_1, t_2, t_3, \ldots, t_n$).

10. The interface unit according to claim 1, wherein said time duration of said control periods is between 0.5-20 ms.

11. The interface unit according to claim 10, wherein said time duration of said control periods is approximately 2.5 ms.

12. The interface unit according to claim 5, wherein said functions include one or more of, measuring said at least one variable, processing measured data, performing radio communication with external devices, performing electrical stimulation of tissue, or performing ablation of tissue, and
   wherein said energy source is adapted to energize one or more of said functions.

13. The interface unit according to claim 1, wherein said interface unit is arranged in a transceiver unit adapted to transfer said sensor signal via a wireless connection to an external device.

14. The interface unit according to claim 1, wherein said interface unit is arranged in a connector unit adapted to transfer said sensor signal via a cable connection to an external device.

15. A measurement system, for intravascular measurements of at least one physiological, or other, variable in a living body, comprising:
   a sensor wire, adapted to be inserted into the body, comprising a sensor element arranged in a distal region of said sensor wire;
   an external device, adapted to receive measured data;
   wherein the measurement system comprises an extracorporeale interface unit according to claim 1, adapted to be connected to a proximal end of said sensor wire.

* * * * *